(12) United States Patent
Rosciano et al.

(10) Patent No.: US 9,130,240 B2
(45) Date of Patent: Sep. 8, 2015

(54) IONIC LIQUID, LITHIUM SECONDARY BATTERY ELECTROLYTE COMPRISING THE IONIC LIQUID, AND LITHIUM SECONDARY BATTERY COMPRISING THE ELECTROLYTE

(75) Inventors: Fabio Rosciano, Schaarbeek (IT); Thierry Verbiest, Veltem-Beisem (BE); Guy Koeckelberghs, Korbeek-Dijle (BE); Lieven De Cremer, Leuven (BE)

(73) Assignees: TOYOTA JIDOSHA KABUSHIKI KAISHA, Toyota (JP); KATHOLIEKE UNIVERSITEIT LEUVEN, Leuven (BE)

( * ) Notice: Subject to any disclaimer, the term of this patent is extended or adjusted under 35 U.S.C. 154(b) by 340 days.

(21) Appl. No.: 13/825,418

(22) PCT Filed: Oct. 12, 2010

(86) PCT No.: PCT/JP2010/068228
§ 371 (c)(1),
(2), (4) Date: Apr. 12, 2013

(87) PCT Pub. No.: WO2012/049780
PCT Pub. Date: Apr. 19, 2012

(65) Prior Publication Data
US 2013/0224576 A1    Aug. 29, 2013

(51) Int. Cl.
| | |
|---|---|
| *H01M 10/056* | (2010.01) |
| *H01M 10/39* | (2006.01) |
| *C07D 295/088* | (2006.01) |
| *H01M 10/052* | (2010.01) |
| *H01M 10/0566* | (2010.01) |
| *H01M 10/0525* | (2010.01) |

(52) U.S. Cl.
CPC ......... *H01M 10/056* (2013.01); *C07D 295/088* (2013.01); *H01M 10/052* (2013.01); *H01M 10/0525* (2013.01); *H01M 10/0566* (2013.01); *H01M 10/39* (2013.01); *H01M 10/399* (2013.01); *H01M 2300/0045* (2013.01); *Y02E 60/122* (2013.01)

(58) Field of Classification Search
CPC ............ H01M 10/056; H01M 10/052; H01M 10/0525; H01M 10/0566; H01M 10/399; H01M 2300/0045; Y02E 60/122
See application file for complete search history.

(56) References Cited

U.S. PATENT DOCUMENTS

| | | |
|---|---|---|
| 6,492,064 B1 | 12/2002 | Smart et al. |
| 6,900,313 B2 | 5/2005 | Wasserscheid et al. |
| 2009/0286163 A1 | 11/2009 | Shin et al. |

OTHER PUBLICATIONS

Kim, et al., "An imidazolium based ionic liquid electrolyte for lithium batteries," *Journal of Power Sources*, vol. 195, No. 22, pp. 7639-7643, 2010.

*Primary Examiner* — Laura Weiner
(74) *Attorney, Agent, or Firm* — Oliff PLC

(57) ABSTRACT

The object of the present invention is to provide an ionic liquid having a chiral center in the structure of a cation contained therein, a lithium secondary battery electrolyte includes the ionic liquid, and a lithium secondary battery including the electrolyte 4 Claims, 4 Drawing Sheets

IONIC LIQUID, LITHIUM SECONDARY BATTERY ELECTROLYTE COMPRISING THE IONIC LIQUID, AND LITHIUM SECONDARY BATTERY COMPRISING THE ELECTROLYTE

TECHNICAL FIELD

The present invention relates to an ionic liquid having a chiral center in the structure of a cation contained therein, a lithium secondary battery electrolyte comprising the ionic liquid, and a lithium secondary battery comprising the electrolyte.

BACKGROUND ART

A secondary battery is a battery which is able to provide electricity by converting chemical energy into electrical energy; moreover, it is a battery which is able to store (during charge) chemical energy by converting electrical energy into chemical energy by passing an electric current in a direction that is opposite to the discharge direction. Among secondary batteries, lithium ion batteries have higher energy density when compared to other chemistries such as Lead-Acid, Nickel-Cadmium and Nickel-Metal Hydride, and are thus widely used as a power source for notebook personal computers, cellular phones and other portable devices.

In a lithium secondary battery using graphite (C) as the negative electrode active material, the reaction described by the following formula (I) proceeds at the negative electrode at the time of discharge:

$$Li_xC \rightarrow C + xLi^+ + xe^- \quad (I)$$

In this formula, $0<x<1$.

An electron produced by the formula (I) passes through an external circuit, which acts as an external load, and then reaches the positive electrode. At the same time, a lithium ion ($Li^+$) produced by the formula (I) is transferred through the electrolyte sandwiched between the negative and positive electrodes from the negative electrode side to the positive electrode side.

When lithium cobaltate ($Li_{1-x}CoO_2$) is used as a positive electrode active material, a reaction described by the following formula (II) proceeds at the positive electrode upon discharge:

$$Li_{1-x}CoO_2 + xLi^+ + xe^- \rightarrow LiCoO_2 \quad (II)$$

In this formula, $0<x<1$.

Upon charging the battery, reactions which are reverse to the reactions represented by the above formulae (I) and (II) proceed at the negative and positive electrodes. The graphite material in which lithium was intercalated ($Li_xC$) becomes reusable at the negative electrode, while lithium cobaltate ($Li_{1-x}CoO_2$) is regenerated at the positive electrode. Because of this, discharge becomes possible again.

Conventional lithium secondary batteries use a flammable, volatile organic compound as an electrolyte solvent; therefore their safety is limited.

As an effort to increase the safety of electrolytic solutions, lithium secondary batteries using an ionic liquid as an electrolyte are conventionally known. An "ionic liquid" is a salt that is liquid at 100° C. or less, and it is generally nonflammable and nonvolatile. Such a nonflammable electrolyte has several advantages, in that it is able to not only increase the safety of the battery but also has a relatively wide potential window (stability range) and shows relatively high ion conductivity.

As an ionic liquid technique, Patent Literature 1 discloses chiral ionic liquids having, as the anion, an anion of an organic or inorganic proton acid and, as the cation, an optically active organic ammonium cation with at least one chirality center and at least one functional group, the chirality center being provided with a distance of up to 5 atomic bonds from the functional group and the functional group being selected from alcohol and so on and able to produce a coordination by forming hydrogen bridges or by providing free electron pairs.

CITATION LIST

Patent Literature

Patent Literature 1: U.S. Pat. No. 6,900,313

SUMMARY OF INVENTION

Technical Problem

On page 3 of Patent Literature 1, it is described that the ionic liquids described in this document can be utilized to separate racemates into individual enantiomers, as solvents for asymmetric inorganic and organic synthesis, and also as solvent for asymmetric catalysis in organic and inorganic reactions. In Patent Literature 1, however, there is no description or suggestion that the ionic liquids described in this document can be utilized for lithium secondary batteries.

The present invention was achieved in view of the aforementioned circumstances, and an object of the present invention is to provide an ionic liquid having a chiral center in the structure of a cation contained therein, a lithium secondary battery electrolyte comprising the ionic liquid, and a lithium secondary battery comprising the electrolyte.

Solution to Problem

The ionic liquid of the present invention is an ionic liquid comprising a cation and a counter anion thereof, wherein the cation has an asymmetric carbon atom to which a positively-charged group and three different substituents selected from the group consisting of a hydrogen atom and an alkyl group having 1 to 10 carbon atoms are bonded, and wherein the content of one enantiomer in the cation is higher than that of the other enantiomer in the cation.

In the ionic liquid of the present invention, the cation preferably has an asymmetric carbon atom to which the positively-charged group and a hydrogen atom, a methyl group and an ethyl group are bonded because when the substituents bonded to the asymmetric carbon atom are small, the ionic liquid is low viscosity and thus the ion conductivity of the ionic liquid can be increased.

In the ionic liquid of the present invention, the positively-charged group preferably has no asymmetric center.

In the ionic liquid of the present invention, the positively-charged group is preferably a group comprising at least one substituent selected from the group consisting of a pyrrolidinium group, a pyridinium group, an imidazolium group and an alkylammonium group.

In the ionic liquid of the present invention, the cation is preferably an N-methyl-N-(2-methylbutyl)pyrrolidinium cation.

In the ionic liquid of the present invention, the cation is preferably an N-methyl-N—(S)-(2-methylbutyl)pyrrolidinium cation.

In the ionic liquid of the present invention, the counter anion is preferably at least one anion selected from the group consisting of a fluoride ion (F−), a chloride ion (Cl−), a bromide ion (Br−), an iodide ion (I−), a tetrafluoroborate ion ($BF_4^-$) and a bis(trifluoromethanesulfonyl)imide ion ([N($SO_2CF_3$)$_2$]−).

In the ionic liquid of the present invention, the cation preferably has an enantiomeric excess of 0 to 100%.

The lithium secondary battery electrolyte of the present invention is a lithium secondary battery electrolyte comprising the above-mentioned ionic liquid.

The lithium secondary battery of the present invention is a lithium secondary battery comprising at least a positive electrode, a negative electrode and an electrolyte that is present between the positive and negative electrodes, wherein the electrolyte is the above-mentioned lithium secondary battery electrolyte.

Advantageous Effects of Invention

According to the present invention, by containing a chiral cation, the electrolyte is provided with a lower melting point than the ionic liquid; instead it rather vitrifies. As a result, according to the present invention, anionic liquid which maintains its liquid state in a wide range of temperatures is obtained. Also according to the present invention, by using such an ionic liquid as a lithium secondary battery electrolyte, the ion conductivity of the electrolyte at low temperature can be increased.

BRIEF DESCRIPTION OF DRAWINGS

In the accompanying drawings and graphs.

DESCRIPTION OF EMBODIMENTS

1. Ionic Liquid

Figure 1:
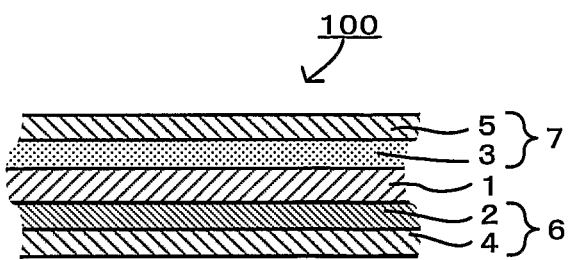
FIG. 1 shows an example of the layered structure of the lithium secondary battery according the present invention and is a schematic view showing a section of the battery cut across the laminating direction.

The ionic liquid of the present invention is an ionic liquid comprising a cation and a counter anion thereof, wherein the cation has an asymmetric carbon atom to which a positively-charged group and three different substituents selected from the group consisting of a hydrogen atom and an alkyl group having 1 to 10 carbon atoms are bonded, and wherein the content of one enantiomer in the cation is possibly higher than that of the other enantiomer in the cation.

In general, as the electrolyte for lithium secondary batteries, a solution produced by dissolving a lithium salt such as $LiPF_6$ in an organic solvent such as ethylene carbonate or dimethyl carbonate or a mixture thereof, is used. This solution has the property of forming a solid ion conductive layer, known as the solid electrolyte interphase (hereinafter referred to as SEI) layer and thus protecting electrodes upon charge and discharge. Other materials having such a property are not known yet. This solution has an ion conductivity of more than 10 mS/cm at room temperature and allows lithium secondary batteries to produce high output power. The solution has a melting point of around −20° C., however. When lithium secondary batteries are cooled to less than the freezing point of the electrolyte, the solution is frozen and the lithium ion conductivity of the same is decreased to one five-hundredth of the conductivity of the same at room temperature. As just described, the freezing of the solution in a low temperature condition decreases battery performance dramatically. Accordingly, to increase the performance in a low temperature condition without deteriorating the same in a room temperature condition, it is necessary to add an additive to the electrolyte.

In recent years, ionic liquids have been drawing attention as an electrolyte since they are less volatile and flammable than organic solvents, and when synthesized their properties can be readily controlled by changing a substituent on the cationic center.

The inventors of the present invention found out that by using a chiral cation having an asymmetric carbon atom as the cation of an ionic liquid and by making the content of one enantiomer in the cation higher than that of the other enantiomer, the electrolyte exhibits a lower melting point than the ionic liquid comprising a racemic mixture of the cation, and they completed the present invention.

The ionic liquid of the present invention can maintain its liquid state in a wide range of temperatures, and when it is used as a lithium secondary battery electrolyte, the ion conductivity of the electrolyte at a low temperature can be increased.

The cation used in the present invention has an asymmetric carbon atom to which a positively-charged group and three different substituents selected from the group consisting of a hydrogen atom and an alkyl group having 1 to 10 carbon atoms are bonded.

To provide a low melting point to the electrolyte, the cation used in the present invention is preferably selected from those having low molecular weights. In particular, the molecular weight of the cation used in the present invention is preferably 130 to 200.

It is more preferable that the cation used in the present invention has an asymmetric carbon atom to which the positively-charged group and a hydrogen atom, a methyl group and an ethyl group are bonded because when the substituents bonded to the asymmetric carbon atom are small, the ionic liquid has low viscosity and thus the ion conductivity of the ionic liquid can be increased.

The positively-charged group preferably has no asymmetric center.

In particular, the positively-charged group is preferably a group comprising at least one substituent selected from the group consisting of a pyrrolidinium group, a pyridinium group, an imidazolium group and an alkylammonium group.

As the cation which meets all of the above conditions, the cation used in the present invention is preferably an N-methyl-N-(2-methylbutyl) pyrrolidinium cation. It is more preferably an N-methyl-N—(S)-(2-methylbutyl)pyrrolidinium cation having an absolute configuration represented by the following formula (1):

[Chemical formula 1]

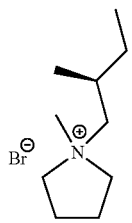

Formula (1)

The cation used in the present invention preferably has an enantiomeric excess of 0 to 100%.

The counter anion used in the present invention is not particularly limited and there may be mentioned those that are normally used as the anion of an ionic liquid. As the counter anion contained in the ionic liquid of the present invention, in particular, there may be mentioned a halide anion such as $Cl^-$, $Br^-$ and $I^-$, a boride anion such as $BF_4^-$, $B(CN)_4^-$ and $B(C_2O_4)_2^-$, an amide anion or imide anion such as $(CN)_2N^-$, $[N(CF_3)_2]^-$ and $[N(SO_2CF_2)_2]^-$, a sulfite anion or sulfate anion such as $RSO_3^-$ (hereinafter, R refers to an aliphatic hydrocarbon group or aromatic hydrocarbon group), $RSO_4^-$, $RfSO_3^-$ (hereinafter, $R^f$ refers to a fluorine-containing halogenated hydrocarbon group) and $R^fSO_4^-$, a phosphate anion such as $R'_2P(O)O^-$, $PF_6^-$ and $R'_3PF_3^-$, $SbF_6^-$, a lactate anion, a nitrate anion, a trifluoroacetate anion, etc.

Of these anions, the counter anion used in the present invention is preferably a fluoride ion ($F^-$), a chloride ion ($Cl^-$), a bromide ion ($Br^-$), an iodide ion ($I^-$), a tetrafluoroborate ion ($BF_4^-$) or a bis(trifluoromethanesulfonyl) imide ion ($[N(SO_2CF_3)_2]^-$).

To have a low melting point, the ionic liquid of the present invention preferably has a low molecular weight. In particular, the ionic liquid of the present invention preferably has a molecular weight of 149 to 580.

2. Lithium Secondary Battery Electrolyte

The lithium secondary battery electrolyte of the present invention comprises the above-mentioned ionic liquid.

The lithium secondary battery electrolyte of the present invention is present between the positive and negative electrode active material layers of the below-mentioned lithium secondary battery. It functions to exchange lithium ions between the electrode layers.

In addition to the ionic liquid, the lithium secondary battery electrolyte of the present invention is allowed to contain an aqueous electrolyte and a non-aqueous electrolyte.

As the non-aqueous electrolyte, there may be used a non-aqueous electrolyte solution or non-aqueous gel electrolyte.

The non-aqueous electrolyte solution for lithium secondary batteries generally contains a lithium salt and a non-aqueous solvent. As the lithium salt, for example, there may be mentioned an inorganic lithium salt such as $LiPF_6$, $LiBF_4$, $LiClO_4$ and $LiAsF_6$, an organic lithium salt such as $LiCF_3SO_3$, $LiN(SO_2CF_3)_2$(Li-TFSI), $LiN(SO_2C_2F_5)_2$ and $LiC(SO_2CF_3)_3$. As the non-aqueous solvent, for example, there may be mentioned ethylene carbonate (EC), propylene carbonate (PC), dimethyl carbonate (DMC), diethyl carbonate (DEC), ethyl methyl carbonate (EMC), ethyl carbonate, butylene carbonate, γ-butyrolactone, sulfolane, acetonitrile, 1,2-dimethoxyethane, 1,3-dimethoxypropane, diethyl ether, tetrahydrofuran, 2-methyltetrahydrofuran, and mixtures thereof. The non-aqueous solvent is preferably a solvent with high oxygen solubility, so that dissolved oxygen can be efficiently used for reaction. The concentration of the lithium salt in the non-aqueous electrolyte solution is in the range of 0.5 mol/L to 3 mol/L, for example.

The non-aqueous gel electrolyte used in the present invention is normally a gelled non-aqueous electrolyte produced by adding a polymer to a non-aqueous electrolyte solution. For example, the non-aqueous gel electrolyte for lithium secondary batteries can be obtained by adding a polymer such as polyethylene oxide (PEO), polyacrylonitrile (PAN) and polymethyl methacrylate (PMMA) to the above-mentioned non-aqueous electrolyte solution to gel. In the present invention, a non-aqueous, gelled $LiTFSI(LiN(CF_3SO_2)_2)$-PEO based electrolyte is preferably used.

As the aqueous electrolyte used for lithium secondary batteries, a mixture of water and a lithium salt is generally used. As the lithium salt, for example, there may be mentioned a lithium salt such as LiOH, LiCl, $LiNO_3$ and $CH_3CO_2Li$.

3. Lithium Secondary Battery

The lithium secondary battery of the present invention is a lithium secondary battery comprising at least a positive electrode, a negative electrode and an electrolyte that is present between the positive and negative electrodes, wherein the electrolyte is the above-mentioned lithium secondary battery electrolyte.

FIG. 1 shows an example of the layered structure of the lithium secondary battery according the present invention and is also a schematic view showing a section of the battery cut across the laminating direction. The lithium secondary battery of the present invention is not limited to this example, however.

Lithium secondary battery 100 comprises positive electrode 6, negative electrode 7 and electrolyte 1. Positive electrode 6 comprises positive electrode active material layer 2 and positive electrode current collector 4. Negative electrode 7 comprises negative electrode active material layer 3 and negative electrode current collector 5. Electrolyte 1 is sandwiched between positive electrode 6 and negative electrode 7.

Among the components of the lithium secondary battery of the present invention, the electrolyte is described above. Hereinafter, other components of the same will be described in detail, which are a positive electrode, a negative electrode, a separator and a battery case.

(Positive Electrode)

The positive electrode of the lithium secondary battery of the present invention preferably comprises a positive electrode active material layer comprising a positive electrode active material. In addition to this, it generally comprises a positive electrode current collector and a positive electrode lead that is connected to the positive electrode current collector. When the lithium secondary battery of the present invention is a lithium-air battery, in place of the positive electrode, the battery has an air electrode comprising an air electrode layer.

(Positive Electrode Active Material Layer)

An embodiment will be described hereinafter, in which an electrode comprising a positive electrode active material layer is employed as the positive electrode.

As the positive electrode active material used in the present invention, in particular, there may be mentioned $LiCoO_2$, $LiNi_{1/3}Mn_{1/3}Co_{1/3}O_2$, $LiNiPO_4$, $LiMnPO_4$, $LiNiO_2$, $LiMn_2O_4$, $LiCoMnO_4$, $Li_2NiMn_3O_8$, $Li_3Fe_2(PO_4)_3$, $Li_3V_2(PO_4)_3$, etc. Of these, $LiCoO_2$ is preferably used as the positive electrode active material in the present invention.

The thickness of the positive electrode active material layer of the present invention varies depending on the intended application of the lithium secondary battery. However, it is preferably in the range of 10 μm to 250 μm, particularly preferably in the range of 20 μm to 200 μm, most preferably in the range of 30 μm to 150 μm.

The average particle diameter of the positive electrode active material is, for example, in the range of 1 μm to 50 μm, preferably in the range of 1 μm to 20 μm, particularly preferably in the range of 3 μm to 5 μm. This is because it could be difficult to handle the positive electrode active material when the average particle diameter of the material is too small, and it could be difficult to make the positive electrode active material layer a flat layer when the average particle diameter of the positive electrode active material is too large. The average particle diameter of the positive electrode active material can be obtained by, for example, measuring the diameter of particles comprising an active material carrier observed with a scanning electron microscope (SEM) and averaging the thus-obtained diameters.

The positive electrode active material layer can comprise a conducting material, a binder, etc., as needed.

The conducting material contained in the positive electrode active material layer used in the present invention is not particularly limited as long as it can increase the conductivity of the positive electrode active material layer. For example, there may be mentioned carbon black such as acetylene black and ketjen black. The content of the conducting material in the positive electrode active material layer varies depending on the type of conducting material, and it is normally in the range of 1% by mass to 10% by mass.

As the binder contained in the positive electrode active material layer used in the present invention, there may be mentioned polyvinylidene fluoride (PVDF) and polytetrafluoroethylene (PTFE), for example. The content of the binder in the positive electrode active material layer can be an amount which can fix the positive electrode active material, etc., and it is preferably as small as possible. The content of the binder is normally in the range of 1% by mass to 10% by mass.

(Positive Electrode Current Collector)

The positive electrode current collector used in the present invention functions to collect current from the positive electrode active material layer. As the material for the positive electrode current collector, for example, there may be mentioned aluminum, stainless steel (SUS), nickel and titanium. Of these, aluminum and SUS are preferred. As the form of the positive electrode current collector, there may be mentioned a foil form, a plate form and a mesh form, for example. Among them, a foil form is preferred.

The electrode active material layer of at least one of the positive and negative electrodes can contain a mixture of at least an electrode active material and a solid electrolyte material. In this case, as the solid electrolyte material, there may be used a solid oxide electrolyte or solid sulfide electrolyte, the above-mentioned polymer electrolyte or gel electrolyte, or the like.

The method for producing the positive electrode used in the present invention is not particularly limited as long as it is a method that gives the above-mentioned positive electrode. After the positive electrode active material layer is formed, the layer can be pressed to increase electrode density.

(Air Electrode Layer)

An embodiment will be described hereinafter, in which an air electrode comprising an air electrode layer is employed as the positive electrode. The air electrode layer used in the present invention comprises at least a conductive material. In addition, it can contain at least one of a catalyst and a binder as needed.

The conductive material used for the air electrode layer of the present invention is not particularly limited as long as it is conductive. For example, there may be mentioned a carbon material. The carbon material can be porous or non-porous. It is preferably porous in the present invention, so that it has a large specific surface area and offers many reaction sites. As the porous carbon material, in particular, there may be mentioned mesoporous carbon, etc. As the non-porous carbon, in particular, there may be mentioned graphite, carbon black, carbon nanotube, carbon fiber, etc. The content of the conductive material in the air electrode layer is in the range of 65% by mass to 99% by mass for example, preferably in the range of 75% by mass to 95% by mass. This is because when the conductive material content is too small, the area of reaction sites is decreased and battery capacity could be decreased, and when the conductive material content is too large, the content of the catalyst becomes relatively small and poor catalyst performance could be obtained.

As the catalyst used for the air electrode layer of the present invention, for example, there may be mentioned cobalt phthalocyanine and manganese dioxide. The content of the catalyst in the air electrode layer is in the range of 1% by mass to 30% by mass for example, preferably in the range of 5% by mass to 20% by mass. This is because when the catalyst content is too small, poor catalyst performance could be obtained, and when the catalyst content is too large, the conductive material content becomes relatively small, so that the area of reaction sites is decreased and battery capacity could be decreased.

From the viewpoint of smooth electrode reaction, the conductive material preferably supports the catalyst.

The air electrode layer only has to contain at least the conductive material. However, it is more preferable that the air electrode layer further contains a binder for fixing the conductive material. As the binder, for example, there may be mentioned polyvinylidene fluoride (PVDF) and polytetrafluoroethylene (PTFE). The content of the binder in the air electrode layer is not particularly limited and is 30% by mass or less for example, preferably in the range of 1% by mass to 10% by mass.

The thickness of the air electrode layer varies depending on the intended use of the air battery, etc. However, it is in the range of 2 μm to 500 μm for example, preferably in the range of 5 μm to 300 μm.

(Air Electrode Current Collector)

The air electrode current collector used in the present invention functions to collect current from the air electrode layer. The material for the air electrode current collector is not particularly limited as long as it is conductive. For example, there may be mentioned stainless-steel, nickel, aluminum, titanium and carbon. As the form of the air electrode current collector, there may be mentioned a foil form, a plate form and a mesh (grid) form, for example. Of these, in the present invention, the air electrode current collector is preferably in a mesh form. This is because the collector in such a form has excellent current collection efficiency. In this case, normally, the air electrode current collector in a mesh form is provided inside the air electrode layer. In addition, the secondary battery of the present invention can comprise a different air electrode current collector (such as a current collector in a foil form) that collects current collected by the air electrode current collector in a mesh form. Also in the present invention, the below-mentioned battery case can also function as the air electrode current collector.

The thickness of the air electrode current collector is in the range of 10 μm to 1,000 μm for example, preferably in the range of 20 μm to 400 μm.

(Negative Electrode)

The negative electrode in the lithium secondary battery of the present invention preferably comprises a negative electrode active material layer comprising a negative electrode active material. In addition to this, it generally comprises a negative electrode current collector and a negative electrode lead that is connected to the negative electrode current collector.

(Negative Electrode Active Material Layer)

The negative electrode layer in the lithium secondary battery of the present invention comprises a negative electrode active material. The negative electrode active material used for the negative electrode active material layer is not particularly limited as long as it can store and release a lithium ion. For example, there may be mentioned metallic lithium, a lithium-containing alloy, a lithium-containing metal oxide, a lithium-containing metal sulfide, a lithium-containing metal nitride and a carbonaceous material such as graphite. The negative electrode active material can be in a powder form or in a thin film form.

As the lithium-containing alloy, for example, there may be mentioned a lithium-aluminum alloy, a lithium-tin alloy, a lithium-lead alloy and a lithium-silicon alloy. As the lithium-containing metal oxide, for example, there may be mentioned a lithium-titanium oxide. As the lithium-containing metal nitride, for example, there may be mentioned a lithium-cobalt nitride, a lithium-iron nitride and a lithium-manganese nitride. Also, a solid electrolyte-coated metallic lithium foil can be used for the negative electrode layer.

The negative electrode layer can comprise a negative electrode active material only, or it can comprise at least one of a conductive material and a binder in addition to the negative electrode active material. For example, when the negative electrode active material is in the form of a foil, the negative electrode layer can be a negative electrode layer comprising a negative electrode active material only. When the negative electrode active material is in the form of powder, it can be a negative electrode layer comprising a negative electrode active material and a binder. The description of the conductive material and binder are omitted here since they are the same as the description described above under "Air electrode layer".

The thickness of the negative electrode active material layer is not particularly limited and is in the range of 10 μm to 100 μm for example, preferably in the range of 10 μm to 50 μm.

(Negative Electrode Current Collector)

The material and form of the negative electrode current collector can be the same as those of the positive electrode current collector described above.

(Separator)

When the battery of the present invention has a structure of stacked laminates each of which comprising a positive electrode, an electrolyte and a negative electrode in this order (positive electrode-electrolyte-negative electrode), it is preferable from the viewpoint of safety to provide a separator between positive and negative electrodes. As the separator, for example, there may be mentioned a porous film such as polyethylene and polypropylene, and a nonwoven fabric such as resin nonwoven fabric and glass fiber tissue.

The materials which can be used for the separator can be also used as an electrolyte support by being impregnated with the above-mentioned electrolyte.

(Battery Case)

The lithium secondary battery of the present invention generally comprises a battery case for housing the positive electrode, electrolyte, negative electrode, and so on. As the form of the battery case, in particular, there may be mentioned a coin form, a prismatic form, a cylinder form and a laminate form, for example.

When the battery of the present invention is a lithium-air battery, the battery case of the same can be an open-to-the-atmosphere battery case or closed battery case. The open battery case is one that has a structure in which at least the air electrode layer can be sufficiently exposed to the air. On the other hand, when the battery case is a closed battery case, it is preferable to provide gas (air) inlet and outlet tubes to the closed battery case. In this case, it is preferable that the gas introduced/emitted through the tubes has a high oxygen concentration, and it is more preferable that the introduced/emitted gas is pure oxygen. Also, it is preferable that the oxygen concentration is high at the time of discharge and low at the time of charge.

EXAMPLES

The present invention will be explained in more detail by way of examples and comparative examples. The scope of the present invention is not limited to these examples, however.

1. Synthesis of N-methyl-N—(S)-(2-methylbutyl)pyrrolidinium bis(trifluoromethanesulfonyl) imide 1-1. Synthesis of (S)-1-bromo-2-methylbutane At first, (S)-1-bromo-2-methylbutane was synthesized by the synthesis method represented by the following formula (2):

[Chemical formula 2]

Formula (2)

To an ice-cold solution of (S)-2-methylbutanol (25 mL, 232 mmol) and triphenyl phosphine (134 g, 511 mmol) in dichloromethane (400 mL), N-bromosuccinimide (86.8 g, 488 mmol) was added in portions under argon atmosphere. After the mixture was stirred overnight at room temperature, the solvent was removed under reduced pressure. Pentane was added to the residue and the insolubilities were removed by filtration and successively washed with pentane. The pentane solution obtained by filtration was dried over $MgSO_4$ and after removing $MgSO_4$ by filtration, the solvent was removed using rotary evaporation. The crude compound was purified by distillation under atmospheric pressure ($T_b$ to 120° C.) and a colorless oil was isolated. The yield was 14.7 g (42%).

The chemical shift in $^1$H-NMR spectrum of (S)-1-bromo-2-methylbutane is as follows.

$^1$H-NMR ($CDCl_3$, 300 MHz): 3.37 (m, 2H), 1.72 (m, 1H), 1.49 (m, 1H), 1.28 (m, 1H), 1.01 (d, 3H), 0.91 (t, 3H).

1-2. Synthesis of N-methyl-N—(S)-(2-methylbutyl)pyrrolidinium bromide

Next, N-methyl-N—(S)-(2-methylbutyl)pyrrolidinium bromide was synthesized by the synthesis method represented by the following formula (3):

[Chemical formula 3]

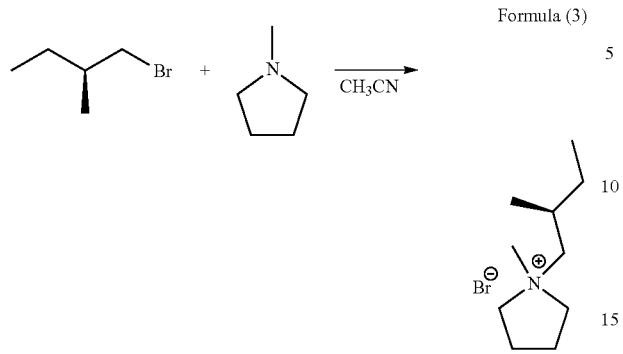

Formula (3)

(S)-1-bromo-2-methylbutane (7.55 g, 50.0 mmol) and N-methylpyrrolidine (4.27 g, 50.1 mmol) were mixed in dry acetonitrile (15 mL) and the resulting solution was stirred at 40° C. during 40 hours under argon atmosphere. The solvent was removed under reduced pressure, thereby obtaining white crystals of N-methyl-N—(S)-(2-methylbutyl)pyrrolidinium bromide. The yield was 11.8 g (100%).

The chemical shift in $^1$H-NMR spectrum of N-methyl-N—(S)-(2-methylbutyl)pyrrolidinium bromide is as follows.

$^1$H-NMR (DMSO-$d_6$, 300 MHz): 3.59 (m, 2H), 3.44 (m, 2H), 3.37 (m, 1H), 3.23 (m, 1H), 3.02 (s, 3H), 2.09 (s, 4H), 2.00 (m, 1H), 1.42 (m, 1H), 1.28 (m, 1H), 1.04 (d, 3H), 0.90 (t, 3H).

1-3. Synthesis of N-methyl-N—(S)-(2-methylbutyl) pyrrolidinium bis(trifluoromethanesulfonyl)imide Then, N-methyl-N—(S)-(2-methylbutyl)pyrrolidinium bis(trifluoromethanesulfonyl)imide was synthesized by the synthesis method represented by the following formula (4):

[Chemical formula 4]

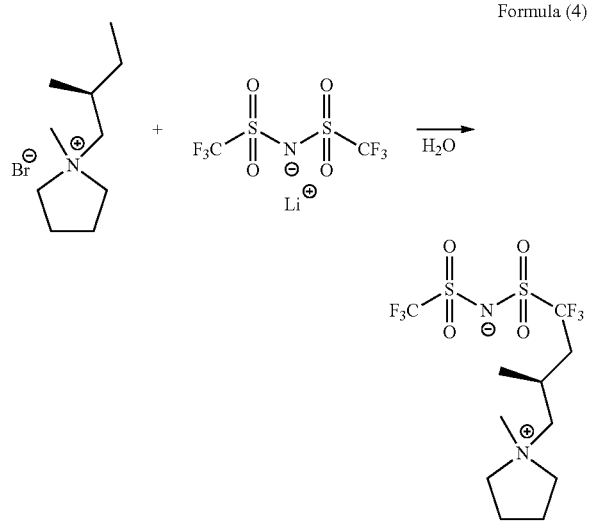

Formula (4)

Equimolar amounts of N-methyl-N—(S)-(2-methylbutyl) pyrrolidinium bromide (11.8 g, 50.0 mmol) and lithium bis (trifluoromethanesulfonyl)imide (14.4 g, 50.0 mmol) were dissolved in distilled water and stirred for 3 hours at room temperature. The product was extracted with dichloromethane and was dried over $MgSO_4$. After removing $MgSO_4$ by filtration, the solvent was removed under reduced pressure, thereby obtaining pale yellow oil. The yield was 20.3 g (93%).

The chemical shift in $^1$H-NMR spectrum of N-methyl-N—(S)-(2-methylbutyl)pyrrolidinium bis(trifluoromethanesulfonyl)imide is as follows.

$^1$H-NMR (DMSO-$d_6$, 300 MHz): 3.54 (m, 2H), 3.40 (m, 2H), 3.32 (m, 1H), 3.18 (m, 1H), 3.00 (s, 3H), 2.10 (s, 4H), 1.97 (m, 1H), 1.43 (m, 1H), 1.29 (m, 1H), 1.05 (d, 3H), 0.91 (t, 3H).

2. Differential scanning calorimetry of N-methyl-N-(S)-(2-methylbutyl)pyrrolidinium bis(trifluoromethanesulfonyl)imide Differential scanning calorimetry (hereinafter referred to as DSC) was performed on the thus-obtained ionic liquid. The detailed condition of DSC is as follows. The apparatus used is a Mettler-Toledo DSC822e module with a heating and cooling rate of 10 K min.$^{-1}$ and a helium atmosphere inside the sample pan. The helium flow is 26 mL min.$^{-1}$; the nitrogen flow is 350 mL min.$^{-1}$.

Figure 2:
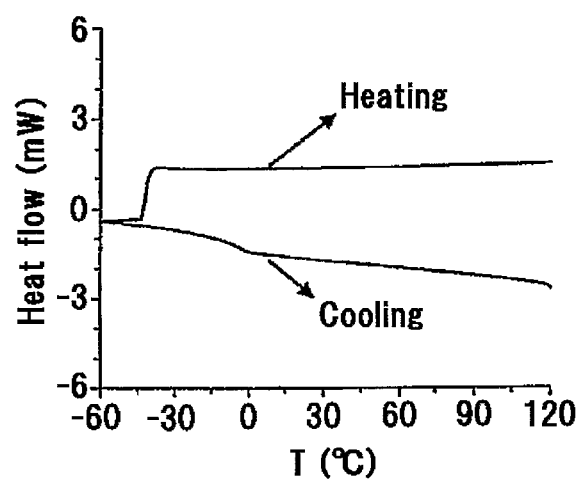
FIG. 2 shows Differential Scanning calorimetry (DSC) curves of N-methyl-N—(S)-(2-methylbutyl)pyrrolidinium bis(trifluoromethanesulfonyl)imide.

FIG. 2 shows DSC curves of N-methyl-N—(S)-(2-methylbutyl)pyrrolidinium bis(trifluoromethanesulfonyl)imide.

No melting nor crystallization were observed between $-60$ and $120°$ C. in the heating or cooling cycle, respectively. However, in the cooling cycle a glass transition is present around $-5°$ C. Nevertheless, the compound is a (very viscuous) liquid at room temperature. As a consequence, it can be concluded that the DSC experiments indicate that the compound does not crystallize at T $>-60°$ C., but instead vitrifies.

3. Measurement of Lithium Ion Conductivity of Electrolytes 3-1. Production of Electrolytes Electrolytes of Examples 1 to 3 and Comparative Examples 1 and 2 were produced by the following methods.

Example 1

Lithium bis(trifluoromethanesulfonyl)imide was added as the supporting salt to the above-mentioned N-methyl-N—(S)-(2-methylbutyl)pyrrolidinium bis(trifluoromethanesulfonyl)imide to a concentration of 0.1 m (mol/kg), thereby obtaining the electrolyte of Example 1.

Example 2

The below-mentioned electrolyte of Comparative Example 2 and the electrolyte of Example 1 were mixed at a ratio of 9:1, thereby obtaining the electrolyte of Example 2.

Example 3

The below-mentioned electrolyte of Comparative Example 2 and the electrolyte of Example 1 were mixed at a ratio of 1:1, thereby obtaining the electrolyte of Example 3.

Comparative Example 1

$LiPF_6$ was added as the supporting salt to a solvent produced by mixing ethylene carbonate and dimethyl carbonate at a mass ratio of 1:1 (hereinafter referred to as EC-DMC) to a concentration of 1 M (mol/L), thereby obtaining the electrolyte of Comparative Example 1.

Comparative Example 2

Lithium bis(trifluoromethanesulfonyl) imide was added as the supporting salt to the above-mentioned EC-DMC to a concentration of 1 M (mol/L), thereby obtaining the electrolyte of Comparative Example 2.

3-2. Measurement of Lithium Ion Conductivity of Electrolytes

Electrochemical impedance spectroscopy was used to measure the lithium ion conductivity of the electrolytes of Examples 1 to 3 and Comparative Examples 1 and 2. The detailed measurement condition is as follows. The measurement by electrochemical impedance spectroscopy was performed after the electrolytes were left at a predetermined measurement temperature for 5 hours or more.

Measuring device: Solartron Analytical Frequency Response Analyzer 1260+Solartron Analytical Electrochemical Interface 1287

Conductivity probe: Conductivity cell with platinum electrodes

Cell constant: $K=0.1$ cm$^{-1}$

Cells filled with the sample electrolytes were placed in a constant-temperature chamber (manufactured by ESPEC Corp.) and the temperature of the chamber was controlled with an accuracy of $\Delta T=\pm 0.1°$ C.

Figure 3:
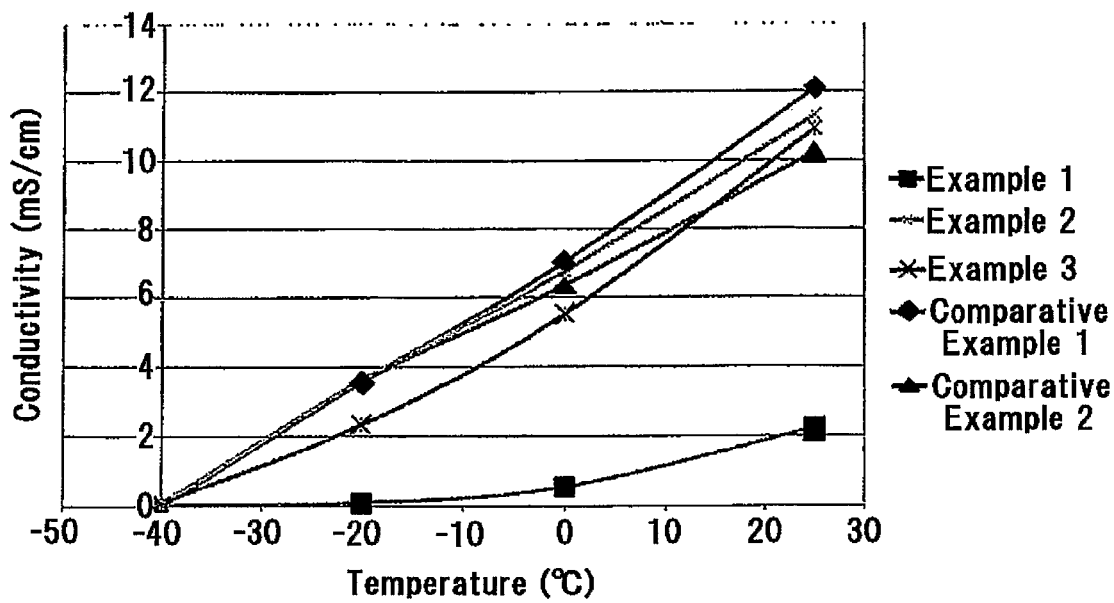
FIG. 3 is a graph showing the lithium ion conductivity change of electrolytes of Examples 1 to 3 and Comparative Examples 1 and 2 in the temperature range of −40° C. to 25° C.
Figure 4:
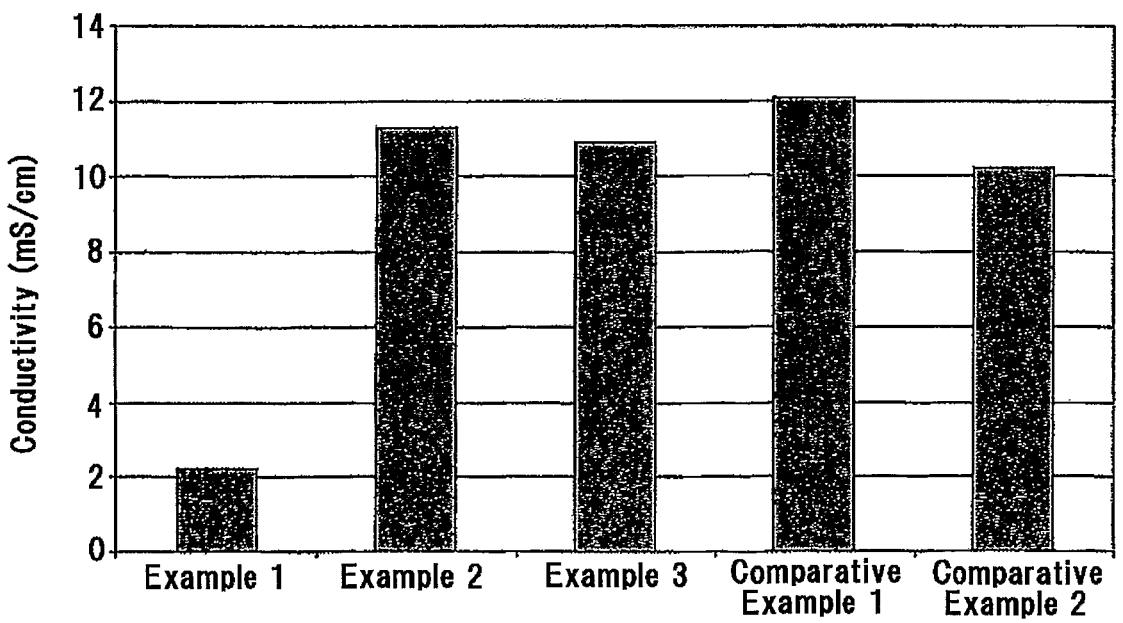
FIG. 4 is a bar graph showing the lithium ion conductivity at 25° C. of the electrolytes of Examples 1 to 3 and Comparative Examples 1 and 2.
Figure 5:
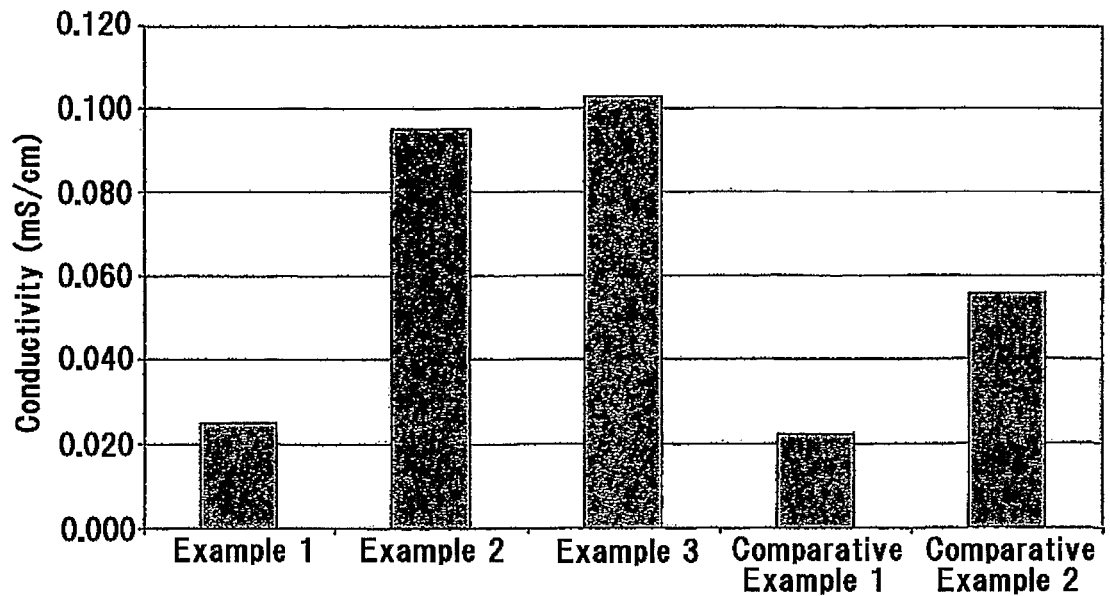
FIG. 5 is a bar graph showing the lithium ion conductivity at −40° C. of the electrolytes of Examples 1 to 3 and Comparative Examples 1 and 2.

FIG. 3 is a graph showing the lithium ion conductivity change of electrolytes of Examples 1 to 3 and Comparative Examples 1 and 2 in the temperature range of $-40°$ C. to $25°$ C. FIG. 4 is a bar graph showing the lithium ion conductivity at $25°$ C. of the electrolytes of Examples 1 to 3 and Comparative Examples 1 and 2. FIG. 5 is a bar graph showing the lithium ion conductivity at $-40°$ C. of the electrolytes of Examples 1 to 3 and Comparative Examples 1 and 2.

As is clear from FIGS. 3 and 4, at $25°$ C., the lithium ion conductivity of Comparative Example 1 is 12 mS/cm and this is the highest of Examples 1 to 3 and Comparative Examples 1 and 2. In contrast, at the same temperature, the lithium ion conductivity of Example 1 is 2 mS/cm and this is the lowest of Examples 1 to 3 and Comparative Examples 1 and 2.

At $25°$ C., however, the lithium ion conductivities of Examples 2 and 3 are more than 10 mS/cm and comparable to Comparative Example 1, the first two examples being prepared by mixing the ionic liquid of the present invention with the carbonates solution (EC-DMC).

On the other hand, as is clear from FIGS. 3 and 5, the lithium ion conductivity of Comparative Example 1 is 0.02 mS/cm at $-40°$ C. and this is the lowest of Examples 1 to 3 and Comparative Example 1. In contrast, at the same temperature, the lithium ion conductivity of Example 1 is 0.025 mS/cm and this is higher than the lithium ion conductivity of Comparative Example 1.

In addition, at $-40°$ C., the lithium ion conductivities of Examples 2 and 3 are about 0.1 mS/cm each and five times the conductivity of Comparative Example 1, the first two examples being prepared by mixing the ionic liquid of the present invention with the carbonates solution (EC-DMC).

Figure 6:
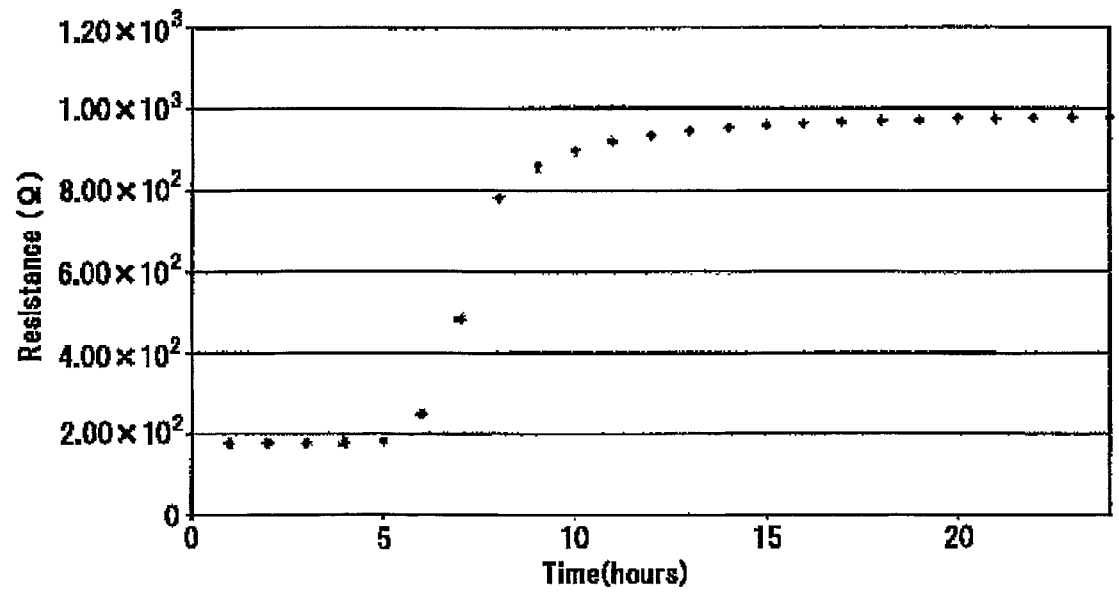
FIG. 6 is a graph showing the resistance change over time of the electrolyte of Example 3 at −40° C.

FIG. 6 is a graph showing the resistance change over time of the electrolyte of Example 3 at $-40°$ C. The resistance was measured every hour for 24 hours.

As is clear from FIG. 6, the electrolyte of Example 3 was not completely frozen even after left at a temperature of $-40°$ C. for less than five hours. The resistance of the same after it was left within 5 hours is less than one-fifth of the resistance of the same after it was left for 24 hours.

Figure 7:
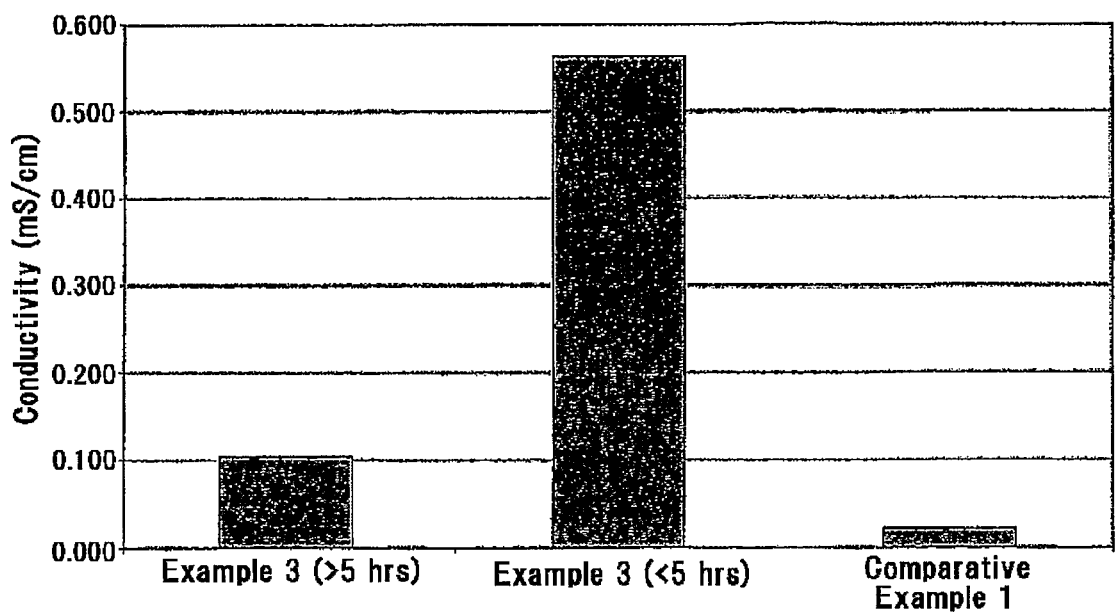
FIG. 7 is a bar graph showing the comparison of lithium ion conductivities of the electrolytes of Example 3 and Comparative Example 1 at −40° C.

FIG. 7 is a bar graph showing the comparison of lithium ion conductivities of the electrolytes of Example 3 and Comparative Example 1 at $-40°$ C. In FIG. 7, the "Example 3 (>5 hrs)" bar shows the result of the electrolyte of Example 3 left at a temperature of $-40°$ C. for more than five hours. The "Example 3 (<5 hrs)" bar shows the result of the same left at a temperature of $-40°$ C. for less than five hours. The "Example 3 (>5 hrs)" and "Comparative Example 1" bars show the same results as those of the "Example 3" and "Comparative Example 1" bars in FIG. 5, respectively.

As is clear from FIG. 7, the lithium ion conductivity of Example 3 which was left at a temperature of $-40°$ C. for more than five hours, is five times the lithium ion conductivity of Comparative Example 1. In addition, the lithium ion conductivity of the same which was left at a temperature of $-40°$ C. for less than five hours, is 25 times the lithium ion conductivity of Comparative Example 1.

4. Summary of Examples

It was found that when mixed with a lithium salt, the ionic liquid of the present invention shows a higher lithium ion conductivity than conventional electrolytes comprising an organic solvent at a temperature of $-40°$ C.

Also, it was found that when added to conventional electrolytes comprising an organic solvent, the ionic liquid of the present invention shows the same lithium ion conductivity as that of the conventional electrolytes at a temperature of $25°$ C.; moreover, at a temperature of $-40°$ C., it shows a lithium ion conductivity that is five times the lithium ion conductivity of the conventional electrolytes. In addition, it was found that when added to conventional electrolytes comprising an organic solvent, even at a temperature of $-40°$ C., the ionic liquid of the present invention shows a lithium ion conductivity that is 25 times the lithium ion conductivity of the conventional electrolytes within 5 hours of exposure to $-40°$ C.

REFERENCE SIGNS LIST

1. Electrolyte
2. Positive electrode active material layer
3. Negative electrode active material layer
4. Positive electrode current collector
5. Negative electrode current collector
6. Positive electrode
7. Negative electrode
100. Lithium secondary battery

The invention claimed is:

1. An ionic liquid comprising a cation and a counter anion thereof,
    wherein the cation is an N-methyl-N—(S)-(2-methylbutyl) pyrrolidinium cation.
2. The ionic liquid according to claim 1, wherein the counter anion is at least one anion selected from the group consisting of a fluoride ion (F$^-$), a chloride ion (Cl$^-$), a bromide ion (Br$^-$), an iodide ion (F$^-$), a tetrafluoroborate ion (BF$_4^-$) and a bis(trifluoromethanesulfonyl)imide ion ([N(SO$_2$CF$_3$)$_2$]$^-$).
3. A lithium secondary battery electrolyte comprising the ionic liquid defined by claim 1.
4. A lithium secondary battery comprising at least a positive electrode, a negative electrode and an electrolyte that is present between the positive and negative electrodes,
    wherein the electrolyte is the lithium secondary battery electrolyte defined by claim 3.

* * * * *